(12) United States Patent
Yang

(10) Patent No.: US 8,524,271 B2
(45) Date of Patent: Sep. 3, 2013

(54) SKIN WOUND DRESSING AND PREPARING METHOD THEREOF

(75) Inventor: Shu-Hui Yang, Kaohsiung (TW)

(73) Assignee: Agricultural Research Institute, Wufeng Taichung (TW)

( * ) Notice: Subject to any disclaimer, the term of this patent is extended or adjusted under 35 U.S.C. 154(b) by 108 days.

(21) Appl. No.: 13/179,793

(22) Filed: Jul. 11, 2011

(65) Prior Publication Data
US 2012/0009241 A1 Jan. 12, 2012

(30) Foreign Application Priority Data
Jul. 12, 2010 (TW) .............................. 99122880 A

(51) Int. Cl.
*A61K 31/715* (2006.01)
*A61K 9/70* (2006.01)
*A61K 9/10* (2006.01)
*A61K 35/78* (2006.01)
*A61P 17/02* (2006.01)

(52) U.S. Cl.
USPC ........... 424/445; 424/488; 424/486; 514/783; 514/866; 514/54; 514/944

(58) Field of Classification Search
USPC ................ 424/445, 486, 488; 514/783, 866, 514/54, 944
See application file for complete search history.

(56) References Cited

U.S. PATENT DOCUMENTS 5,547,672 A * 8/1996 Xiu .......................... 424/195.15
5,635,196 A * 6/1997 Murphy ........................ 424/409
5,658,592 A * 8/1997 Tanihara et al. ............. 424/488

OTHER PUBLICATIONS

Sachin Patil: "Crosslinking of Polysaccharides: methods and Applications", retrieved from internet: http://www.pharmainfo.net/reviews/crosslinking-polysaccharides-methods-and-applications. Retrieved on Jan. 28, 2013.*

* cited by examiner

*Primary Examiner* — Ernest Arnold
*Assistant Examiner* — Hong Yu
(74) *Attorney, Agent, or Firm* — Kirton McConkie; Evan R. Witt

(57) ABSTRACT

A skin wound dressing is disclosed. The skin wound dressing comprises *Tremella* polysaccharide and alginate and is used to cover on a skin wound to accelerate wound healing. The *Tremella* polysaccharide is isolated from a hot water extract of *Tremella fuciformis*. The skin wound dressing is a *Tremella* polysaccharide composite fiber, a *Tremella* polysaccharide sponge or a *Tremella* polysaccharide hydrogel.

17 Claims, No Drawings

SKIN WOUND DRESSING AND PREPARING METHOD THEREOF

FIELD OF THE INVENTION

The present invention relates to a skin wound dressing, and more particularly to a skin wound dressing comprising *Tremella* polysaccharide.

BACKGROUND OF THE INVENTION

The functions of skin include excretion, protection, absorption, regulation and sensory perception. When there is a wound on the skin, the skin may not have normal functions and the appearance of the skin is affected, and even more, an infection may be caused.

The wound healing process includes three phases: inflammation, proliferation and maturation. The symptoms of the inflammation phase include red coloration, swelling and burning sensations, and may continue for three to four days, and even one week. During the proliferation phase, granulation tissues start to grow, thin epidermal cell layers grow into the wound area, new blood vessels develop and the wound contracts, and the proliferation phase continues for ten days to two weeks. During the maturation phase, the scar forms and the wound area decreases, and the maturation phase continues for two weeks to six months. The complete healing of the wound usually takes two years.

The skin wound dressing is used to cover the wound, prevent infection, accelerate wound healing, ease pain and prevent scar formation. Therefore, the present invention provides a new skin wound dressing to become a new choice in the market.

SUMMARY OF THE INVENTION

An object of the present invention is to provide a skin wound dressing for effectively accelerating wound healing and preventing scar formation.

According to an aspect of the present invention, there is provided a skin wound dressing comprising *Tremella* polysaccharide and alginate for covering on a skin wound to accelerate wound healing.

In an embodiment, the *Tremella* polysaccharide is isolated from a hot water extract of *Tremella fuciformis*, the *Tremella* polysaccharide is an acid heteropolysaccharide, the *Tremella* polysaccharide has a linear backbone of α-(1→3)-D-mannan, substituted with β-D-xylose, β-D-glucuronic acid and β-(1→2)-D-xylobiose at C2 position of mannose residue, and the *Tremella* polysaccharide has a molecular weight of 200-1600 kilodaltons.

In an embodiment, the skin wound dressing is *Tremella* polysaccharide composite fiber, *Tremella* polysaccharide sponge or *Tremella* polysaccharide hydrogel, wherein the *Tremella* polysaccharide composite fiber is formed by cross-linking between the *Tremella* polysaccharide and the alginate. Preferably, the *Tremella* polysaccharide composite fiber is *Tremella* polysaccharide non-woven fabric.

In an embodiment, the alginate is sodium alginate.

According to another aspect of the present invention, there is provided a method for preparing a skin wound dressing, comprising steps of providing a *Tremella* polysaccharide, wherein the *Tremella* polysaccharide is isolated from a hot water extract of *Tremella fuciformis*; and mixing the *Tremella* polysaccharide with an alginate to form the skin wound dressing.

The above objects and advantages of the present invention will become more readily apparent to those ordinarily skilled in the art after reviewing the following detailed description.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The present invention provides a new use of *Tremella* polysaccharide for skin wound dressing to accelerate wound healing. The *Tremella* polysaccharide is isolated from the *Tremella* mushroom including but not limited to *Tremella fuciformis* (Berk), *Tremella mesenterica*, *Tremella aurantia*, and *Tremella encepuala*.

In order to obtain a more natural extract of *Tremella* mushroom, a physical method is used to extract the active polysaccharide in the present invention without adding any chemical agent. The method is described as follows. First, a raw material of the fruiting bodies of *Tremella fuciformis* is rinsed with water. Subsequently, a suitable amount of water is added to the raw material, and then heated to 80-175° C. to extract the polysaccharide in hot water. After the hot water extraction for about 0.5-4 hours, it is centrifuged at 3000-5000 rpm for about 2-5 minutes to obtain a polysaccharide solution, which is colorless, transparent, odorless, tasteless, and viscous. Besides, the residues can be resuspended in the water and then heated and centrifuged as the above steps to obtain more polysaccharide extracts.

The extracted *Tremella* polysaccharide is glucuronoxylomannan, an acid heteropolysaccharide, having a linear backbone of α-(1→3)-D-mannan, substituted with β-D-xylose, β-D-glucuronic acid and β-(1→2)-D-xylobiose at C2 position of mannose residue, and its molecular weight is 200-1600 kilodaltons. This high-molecular substance shows good viscosity at temperature of 1-100° C. and can be stored for a long period of time. The extracted *Tremella* polysaccharide is mild to our skin; when it is applied to the skin, it makes the skin soft and tender and has excellent moisturizing effect. In addition, the results of cell viability assay and biocompatibility test show that the extracted *Tremella* polysaccharide does not inhibit cell growth, so it has no cytotoxicity, and has good biocompatibility.

The extracted *Tremella* polysaccharide is further used to form a skin wound dressing by mixing the *Tremella* polysaccharide with high molecular natural polysaccharide, so as to form a biodegradable skin wound dressing such as *Tremella* polysaccharide composite fiber, *Tremella* polysaccharide non-woven fabric, *Tremella* polysaccharide sponge or *Tremella* polysaccharide hydrogel. The high molecular natural polysaccharide is a neutral polysaccharide, a basic polysaccharide or an acidic polysaccharide. For example, the neutral polysaccharide includes cellulose, dextran and starch, the basic polysaccharide includes chitin and chitosan, and the acidic polysaccharide includes alginic acid and hyaluronic acid. The high molecular natural polysaccharide also includes glycosaminoglycans, such as chondroitin sulfate and heparin sulfate.

The following embodiments illustrate the method for preparing the *Tremella* polysaccharide composite fiber and non-woven, the *Tremella* polysaccharide sponge and the *Tremella* polysaccharide hydrogel by mixing the *Tremella* polysaccharide with alginic acid as an example, but it is not intended to limit the present invention to the precise form disclosed.

Example 1

Preparation of *Tremella* Polysaccharide Composite Fiber and Non-Woven Fabric 0.1-1.0% *Tremella* polysaccharide solution and 2.0-8.0% alginate (such as sodium alginate) solution are mixed in a volume ratio of 4:1 to obtain a spinning solution of *Tremella* polysaccharide and alginate mix. Next, a wet spinning process is performed to the spinning solution, so as to form a *Tremella* polysaccharide composite fiber having high mechanical strength by means of the cross-linking between the *Tremella* polysaccharide and alginate. Further, the *Tremella* polysaccharide composite fiber is processed by a carding machine to form thin fiber webs, and then processed by a laminating machine for overlapping the thin fiber webs to form a thick fiber web in a rectangular shape. Then the thick fiber web is processed by a needle punching machine to form a *Tremella* polysaccharide non-woven fabric having a basis weight of 150 g/m$^2$, which can be further cut and sterilized to form a *Tremella* polysaccharide non-woven dressing.

Example 2

Preparation of *Tremella* Polysaccharide Sponge 0.1-1.0% *Tremella* polysaccharide solution and 2.0-8.0% alginate (such as sodium alginate) solution are mixed in a volume ratio of 4:1 to obtain a mixed solution. The mixed solution is contained in a mold and freeze dried to remove water, and then cut and sterilized to form a *Tremella* polysaccharide sponge.

Example 3

Preparation of *Tremella* Polysaccharide Hydrogel 0.1-1.0% *Tremella* polysaccharide solution and 2.0-8.0% alginate (such as sodium alginate) solution are mixed in a volume ratio of 3:1 to obtain a first solution. Then the first solution is mixed with a gel precursor, such as 0.2-0.8% acrylic gel medium, in a volume ratio of 1:1 to obtain a second solution. The second solution is further illuminated to become a hydrogel, which is then cut and sterilized to form a *Tremella* polysaccharide hydrogel.

Example 4

Animal Test

First, SD rats are marked on their backs to have a square mark of 2 cm×2 cm each. Then the full-thickness skin in the square mark area is surgically excised to form a wound on the back. Then the skin wound dressing of the present invention, such as the *Tremella* polysaccharide non-woven fabric, having a size of 3 cm×3 cm is covered on the wound, and fixed by a surgical tape and an elastic bandage. The wound healing condition is observed and recorded at days 3, 7, 10 and 14 after the surgery, wherein the control group uses the alginate dressing without *Tremella* polysaccharide and the treated group uses the *Tremella* polysaccharide non-woven fabric of the present invention.

From the experiment, it is shown that the body weights and the body weight gains (%) from day 3 to day 14 of the rats between the control group and the treated group have no significant difference ($p>0.05$). While comparing the healing area, as shown in Table 1, the healing areas at day 7 of the control group and the treated group are respectively 59.0±13.0% and 55.2±6.3%, which shows that the healing rate of the treated group is slower than that of the control group in the early healing stage, and the slow healing rate of the treated group in the early healing stage can prevent rapid wound contraction which results in thick scar formation. At day 14, the healing areas of the control group and the treated group are respectively 80.3±5.7% and 90.0±2.7%, wherein the healing area of the treated group is larger than that of the control group and there exists a significant difference ($p<0.05$) therebetween. Therefore, the *Tremella* polysaccharide skin wound dressing of the present invention can effectively accelerate wound healing.

TABLE 1

| Healing Area Assessment | | | |
|---|---|---|---|
| Day | Area (%) | Control | Treated |
| 3 | Residue area$^z$ | 65.9 ± 8.7 | 72.7 ± 3.3 |
|   | Healing area$^y$ | 34.1 ± 8.7 | 27.3 ± 3.3 |
| 7 | Residue area | 41.0 ± 13.0 | 44.8 ± 6.3 |
|   | Healing area | 59.0 ± 13.0 | 55.2 ± 6.3 |
| 10 | Residue area | 27.5 ± 7.1 | 22.0 ± 6.3 |
|    | Healing area | 72.5 ± 7.1 | 78.0 ± 6.3 |
| 14 | Residue area | 19.7 ± 5.7 | 10.0 ± 2.7 |
|    | Healing area | 80.3 ± 5.7 | 90.0 ± 2.7 |

$^z$Residue area (%) is calculated by residual wound area divided with total excised area (2 cm × 2 cm) and then multiplied with 100.
$^y$Healing area (%) is calculated by total excised area minus residual wound area and divided with total excised area and then multiplied with 100.

In addition, at day 14, a tissue slice is made from the skin tissue in the center of the wound, and the cross-section of the skin tissue is analyzed for the pathologic histology assessment. The skin healing morphology is assessed according to the method taught by Altavilla et al. (2001), i.e. epidermal and dermal regeneration, granulation tissue thickness, and angiogenesis are scored as described by Altavilla et al. (2001). The result in Table 2 shows that the scores for epidermal and dermal regeneration, granulation tissue thickness, and angiogenesis of the treated group are all higher than those of the control group. Therefore, from the pathologic histology assessment, the *Tremella* polysaccharide skin wound dressing of the present invention can effectively accelerate wound healing.

TABLE 2

| Pathologic Histology Assessment | | |
|---|---|---|
| Scores | Control | Treated |
| Epidermal and dermal regeneration | 1.8 ± 0.4 | 2.2 ± 0.4 |
| Granulation tissue thickness | 1.6 ± 0.5 | 1.8 ± 0.4 |
| angiogenesis | 1.2 ± 0.4 | 1.4 ± 0.5 |
| Total scores | 4.6 ± 0.5 | 5.4 ± 1.0 |

From the above, the present invention provides a skin wound dressing, which is prepared by mixing the *Tremella* polysaccharide with alginate to form a biodegradable skin wound dressing such as *Tremella* polysaccharide composite fiber, *Tremella* polysaccharide non-woven fabric, *Tremella* polysaccharide sponge or *Tremella* polysaccharide hydrogel. When the skin wound dressing comprising *Tremella* polysaccharide is covered on the skin wound, the healing area is significantly increased and the healing time is thus shortened, so the skin wound dressing of the present invention effectively accelerates wound healing. Moreover, since the *Tremella* polysaccharide has moisturizing effect, so in the early healing stage, it can prevent rapid wound contraction and thus prevent scar formation. Besides, when the wound is in a moist environment, the cell regeneration and migration is faster, so the recover rate is faster than in a dry environment. In conclusion, the present invention provides a new biomedical material which includes the natural, noncytotoxic and biocompatible *Tremella* polysaccharide, and can effectively accelerate wound healing and prevent scar formation.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A skin wound dressing comprising *Tremella* polysaccharide and alginate for covering on a skin wound to accelerate wound healing, wherein the skin wound dressing includes a 0.1-1.0% *Tremella* polysaccharide solution and a 2.0-8.0% alginate solution mixed in a volume ratio ranging from 3:1 to 4:1.

2. The skin wound dressing according to claim 1 wherein the *Tremella* polysaccharide is isolated from a hot water extract of *Tremella fuciformis*.

3. The skin wound dressing according to claim 1 wherein the *Tremella* polysaccharide is an acid heteropolysaccharide.

4. The skin wound dressing according to claim 1 wherein the *Tremella* polysaccharide has a linear backbone of α-(1→3)-D-mannan, substituted with β-D-xylose, β-D-glucuronic acid and β-(1→2)-D-xylobiose at C2 position of mannose residue.

5. The skin wound dressing according to claim 1 wherein the *Tremella* polysaccharide has a molecular weight of 200-1600 kilodaltons.

6. The skin wound dressing according to claim 1 wherein the skin wound dressing is *Tremella* polysaccharide composite fiber, *Tremella* polysaccharide sponge or *Tremella* polysaccharide hydrogel.

7. The skin wound dressing according to claim 6 wherein the *Tremella* polysaccharide composite fiber is formed by cross-linking between the *Tremella* polysaccharide and the alginate.

8. The skin wound dressing according to claim 6 wherein the *Tremella* polysaccharide composite fiber is *Tremella* polysaccharide non-woven fabric.

9. The skin wound dressing according to claim 1 wherein the alginate is sodium alginate.

10. A method for preparing a skin wound dressing, comprising steps of:
   providing a *Tremella* polysaccharide, wherein the *Tremella* polysaccharide is isolated from a hot water extract of *Tremella fuciformis*; and
   mixing the *Tremella* polysaccharide with an alginate to form the skin wound dressing; wherein the skin wound dressing includes a 0.1-1.0% *Tremella* polysaccharide solution and a 2.0-8.0% alginate solution mixed in a volume ratio ranging from 3:1 to 4:1.

11. The method for preparing the skin wound dressing according to claim 10 wherein the *Tremella* polysaccharide is an acid heteropolysaccharide.

12. The method for preparing the skin wound dressing according to claim 10 wherein the *Tremella* polysaccharide has a linear backbone of α-(1→3)-D-mannan, substituted with β-D-xylose, β-D-glucuronic acid and β-(1→2)-D-xylobiose at C2 position of mannose residue.

13. The method for preparing the skin wound dressing according to claim 10 wherein the *Tremella* polysaccharide has a molecular weight of 200-1600 kilodaltons.

14. The method for preparing the skin wound dressing according to claim 10 wherein the skin wound dressing is *Tremella* polysaccharide composite fiber, *Tremella* polysaccharide sponge or *Tremella* polysaccharide hydrogel.

15. The method for preparing the skin wound dressing according to claim 14 wherein the *Tremella* polysaccharide composite fiber is formed by cross-linking between the *Tremella* polysaccharide and the alginate.

16. The method for preparing the skin wound dressing according to claim 14 wherein the *Tremella* polysaccharide composite fiber is *Tremella* polysaccharide non-woven fabric.

17. The method for preparing the skin wound dressing according to claim 10 wherein the alginate is sodium alginate.

* * * * *